United States Patent [19]

Heindl et al.

[11] Patent Number: 5,440,044

[45] Date of Patent: Aug. 8, 1995

[54] LEUKOTRIENE-B₄ DERIVATIVES, PROCESS FOR THEIR PRODUCTION AND THEIR USE AS PHARMACEUTICAL AGENTS

[75] Inventors: Josef Heindl; Werner Skuballa; Bernd Buchmann; Wolfgang Frohlich; Roland Ekerdt; Claudia Giesen, all of Berlin, Germany

[73] Assignee: Schering Aktiengesellschaft, Berlin and Bergkamen, Germany

[21] Appl. No.: 161,074

[22] Filed: Dec. 3, 1993

Related U.S. Application Data

[63] Continuation of Ser. No. 984,011, Nov. 30, 1992, abandoned, which is a continuation of Ser. No. 820,661, Jan. 17, 1992, abandoned filed as PCT/DE91/00249, Mar. 19, 1991.

Foreign Application Priority Data

[30] Mar. 19, 1990 [DE] Germany .................. 40 09 117.1

[51] Int. Cl.⁶ .................. C07D 213/60; C07C 59/48
[52] U.S. Cl. .................. 546/301; 546/309; 546/314; 546/323; 546/340; 546/341; 546/344; 562/470
[58] Field of Search .............. 562/470; 546/301, 309, 546/314, 323, 340, 341, 344

[56] References Cited

FOREIGN PATENT DOCUMENTS

88/05045 7/1988 WIPO .

OTHER PUBLICATIONS

Lin et al., "Novel Molecules that Antagonize Leucotriene B4 Binding to Neutrophils," Ann. N.Y. Acad. Sci., vol. 524, pp. 196–200 (Apr. 9, 1988).
Chemical Abstracts 112:55263z (Feb. 19, 1990).
Morris et al., "Synthesis of Novel Antagonists of Leukotriene B4," Tetrahedron Letters, vol. 29, No. 2, pp. 143–146 (Jan. 1988).
Burgos et al., "Asymmetric Synthesis of the Diastereoisomers of the Leukotriene B4 Antagonist," Tetrahedron Letters, vol. 30, No. 38, pp. 5081–5084 (Oct. 1989). Chem. Abstr. 110(19):172989k; J. Morris; Jul. 14, 1988 PCT; 1989.

Primary Examiner—Johann Richter
Assistant Examiner—Michael B. Hydorn
Attorney, Agent, or Firm—Millen, White, Zelano, & Branigan

[57] ABSTRACT

The present invention relates to a leukotriene-B₄ analog according to formula I

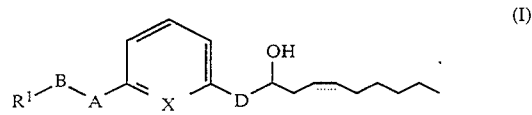

in which
R¹ is a COOR² group, wherein R² is a $C_{2-4}$-alkyl group;
B is a $C_{1-3}$-alkylene group, a radical

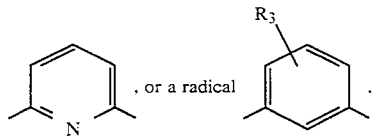 , or a radical wherein R³ is a hydrogen atom or a carboxy or methoxycarbonyl group;

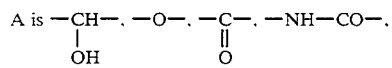

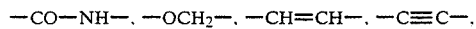

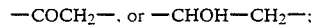

X is N or CH;

D is

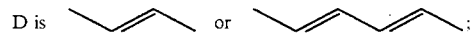

... is a single or double bond; or
optionally, their salts with physiologically compatible bases. The present invention also relates to the production of the latter leukotriene-B₄ analogs and their use as pharmacological agents.

2 Claims, No Drawings

LEUKOTRIENE-B₄DERIVATIVES, PROCESS FOR THEIR PRODUCTION AND THEIR USE AS PHARMACEUTICAL AGENTS

This application is a continuation of application Ser. No. 07/984,011, filed Nov. 30, 1992 now abandoned which is a continuation of application Ser. No. 07/820,661, filed Jan. 17, 1992 now abandoned filed as PCT/DE91/00249, Mar. 19, 1991.

The invention relates to new leukotriene-B₄ derivatives, the process for their production as well as their use as pharmaceutical agents.

Leukotriene B₄ (LTB4) was discovered in 1979 by B. Samuelsson et al. as a metabolite of arachidonic acid. In the biosynthesis, leukotriene A₄ is formed by the enzyme 5-lipoxygenase first as a central intermediate product, which then is converted by a specific hydrolase to the LTB₄.

KEY:
Arachidonsaeure=arachidonic acid
Leukotrien A₄ (LTA4)=leukotriene A₄ (LTA₄)
Glutathion-S-transferase=glutathione-S-transferase
Leukotrien B₄ (LTB4)=leukotriene B₄ (LTB₄)
Leukotrien C₄ (LTC4)=leukotriene C₄ (LTC₄)

try and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that LTB4 is an important inflammation mediator for inflammatory diseases, in which leukocytes invade the affected tissue.

It is known from the LTB₄ that it causes the adhesion of leukocytes on the blood vessel wall. LTB₄ is chemotactically effective, i.e., it triggers a directed migration of leukocytes in the direction of a gradient of increasing concentration. Further, because of its chemotactic activity, it indirectly changes the vascular permeability, and a synergism with prostaglandin E₂ was observed. LTB₄ obviously plays a decisive role in inflammatory, allergic and immunological processes.

Leukotrienes and especially LTB₄ are involved in skin diseases, which accompany inflammatory processes (increased vessel permeability and formation of edemas, cell infiltration), increased-proliferation of skin cells and itching, such as, for example, in eczemas, erythemas, psoriasis, pruritus and acne. Pathologically increased leukotriene concentrations are involved ei-

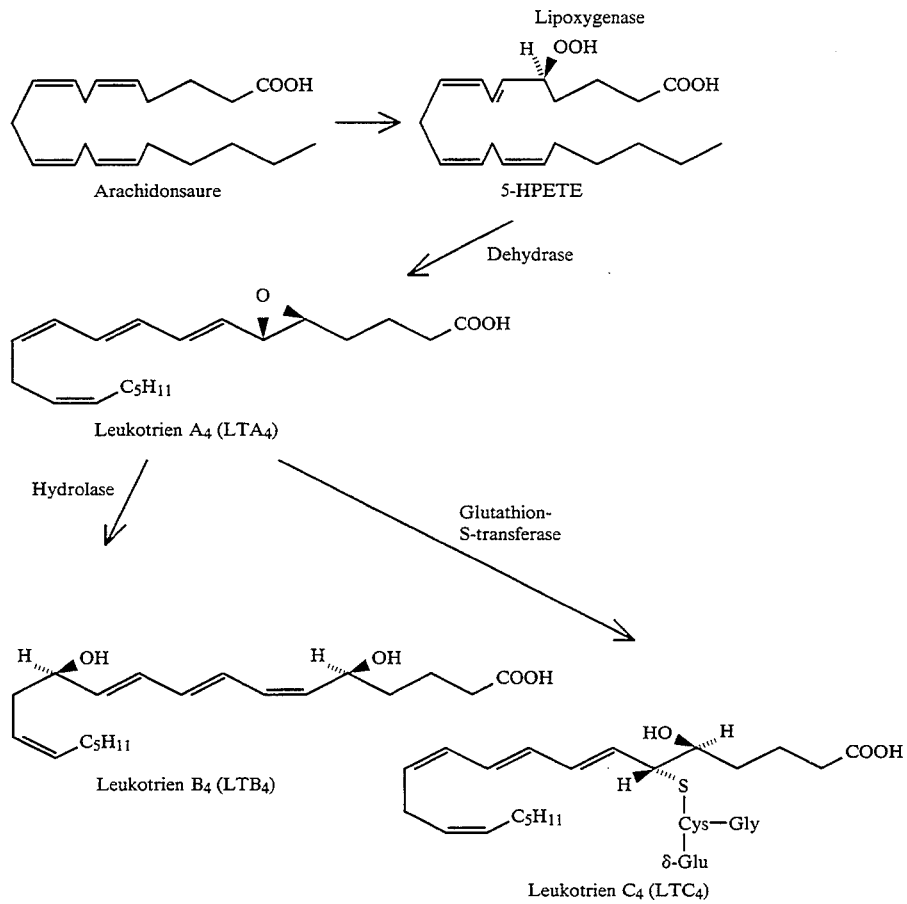

The nomenclature of the leukotrienes can be gathered from the following works:
a) B. Samuelsson et al., Prostaglandins 19, 645 (1980); 17, 785 (1979).
b) C. N. Serhan et al., Prostaglandins 34, 201 (1987).

The physiological and especially the pathophysiological importance of leukotriene B₄ is summarized in several more recent works: a) The Leukotrienes, Chemisther causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and LTB$_4$ are involved especially in arthritis, chronic lung disease (e.g., asthma), rhinitis and inflammatory intestinal diseases.

Antagonists against LTB$_4$ itself or inhibitors of those enzymes which are involved in the synthesis of the LTB$_4$, can be effective as specific medications, especially against diseases which accompany inflammations and allergic reactions.

Besides the therapeutic possibilities, which can be derived from an antagonizing of LTB$_4$ with LTB$_4$ analogs, the usefulness and potential use of leukotriene-B$_4$ agonists for the treatment of fungus diseases of the skin was also able to be shown recently (H. Katayama, Prostaglandins 37, 797 (1988)).

Further uses for LTB$_4$ agonists follow from the LTB$_4$-stimulated activation of components of the immunological system with various indications, such as infectious diseases, burn injuries, in the treatment of tumors or, e.g., in the treatment of AIDS. In AIDS patients, e.g., a reduced release of LTB$_4$ in the stimulation of neutrophils was reported. (AIDS, 1989, 3, 651).

The invention relates to new leukotriene-B$_4$ analogs of formula I $$R_1 \diagdown B \diagdown A \diagdown X \diagdown D \diagdown \text{(chain with OH)} \tag{I}$$

in which

R$^1$ means radical COOR$^2$ with R$^2$ meaning a hydrogen atom or a (C$_1$-C$_4$)-alkyl group or R$^1$ means radical CH$_2$OH, B means an alkylene group with 1-3 C atoms in the chain, a

[pyridine ring with N]

or a radical

[phenyl ring with R$_3$]

with R$^3$ meaning a hydrogen atom, a carboxy or alkoxycarbonyl group with 1-4 C atoms in the alkoxy radical, A means groups

—CH—, —O—, —C—, —NH—CO—,
  |              ||
  OH             O

—CO—NH—, —OCH$_2$—, —CH=CH—,

—C≡C—, —COCH$_2$— or —CHOH—CH$_2$—,

X means N or CH,
D means groups

[cis-alkene] or [diene]

and

. . . means a single or double bond, P1 as well as optionally their salts with physiologically harmless bases.

As alkyl groups R$_2$, straight-chain or branched-chain alkyl groups with 1-4 C atoms are suitable, such as, for example, methyl, ethyl, propyl, isopropyl, butyl, isobutyl, tert-butyl.

As preferred alkyl groups R$_2$, those with 1-2 C atoms can be mentioned.

As alkylene group B, straight-chain or branched-chain, saturated alkylene radicals with 1-3 C atoms are suitable. For example, there can be mentioned: the methylene, the ethylene, the 1,2-propylene and especially the trimethylene group.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

The leukotriene-B$_4$ derivatives of formula I form cyclodextrin clathrates with $\alpha$-, $\beta$-, $\gamma$-cyclodextrin.

Especially preferred compounds of this invention are compounds of formula I, in which R$^1$ represents COOH, COOCH$_3$ or COOC$_2$H$_5$,
B represents —(CH$_2$)$_n$— with n=1-3,
A represents groups

—CH—, —O—, —C—, —NH—CO—,
  |              ||
  OH             O

—CO—NH—, —OCH$_2$—

—CH=CH—, —C≡C—, —COCH$_2$—, or —CHOH—CH$_2$—,

X represents N or CH,
D represents groups

[cis-alkene] or [diene]

and
. . . represents a single bond.

The invention further relates to a process for the production of the leukotriene-B$_4$ derivatives of formula I according to the invention, which is characterized in that, in a way known in the art, a) a compound of formula II $$Z \diagdown X \diagdown D \diagdown \text{(chain with OH)} \tag{II}$$

in which D has the above-indicated meaning and . . . represents a single or a double bond and X represents nitrogen and in which Z symbolizes a bromine atom or an iodine atom, is reacted, after reaction with n-butyllithium, with a compound of formula III $$R^1—B—R^4 \quad (III),$$

in which $R^1$ and B have the above-indicated meanings and $R^4$ means radicals —CHO or —COOCH$_3$, or b) a compound of formula IV, (IV)

[Structure: R$_1$—B—A—X—Z with cyclic portion]

in which $R^1$, B, A and Z have the above-indicated meanings and X means nitrogen, is reacted with a tri-n-butylstannane of formula V,

[Structure: (C$_4$H$_9$)$_3$Sn— chain with OH] (V)

in which . . . represents a single or a double bond, in the presence of a palladium catalyst, such as, for example, 1,1'-bis-(diphenylphosphino)-ferrocene-palladium(II) chloride, or c) a phenylene derivative of formula VI,

[Structure: phenyl with CHO, OAc, D substituents and alkyl chain] (VI)

in which D means groups or , Ac means an acyl group with up to 8 C atoms and . . . means a single or a double bond, is reacted with a Grignard compound of general formula VII $$\begin{array}{c} R_5 \\ R_6—SiO—CH_2—B—MgY, \\ R_7 \end{array} \quad (VII)$$

in which B has the above-mentioned meaning, Y represents a chlorine atom or a bromine atom and substituents R$_5$, R$_6$ and R$_7$ are the same or different and mean C$_1$-C$_4$ alkyl groups or phenyl groups, the free hydroxy group is acylated, the silyl ether is cleaved off and the hydroxymethyl compound is optionally oxidized to the carboxyl compound, and present acyl groups are cleaved off and the carboxyl group is esterified or converted to its salts.

Initial compounds II, IV and VI are produced according to the processes indicated in the examples.

The reaction of the compounds of formula II with compounds of formula III takes place in a way known in the art, as indicated in the respective examples. The reaction conditions indicated in them, as far as solvent, temperature and reaction time are concerned, naturally are not limited only to the data in the examples, but they can be modified to a scope that can be duplicated by the average individual skilled in the art. The same applies to the reaction of IV with V or VI with VII.

As silyl ether protecting groups of the Grignard reagent of formula VII, preferably the tert-butyldimethylsilyl group or the tert-butyldiphenylsilyl group is used.

The oxidation of the hydroxy groups is performed according to the methods known to one skilled in the art. As oxidizing agents, for example, pyridinium dichromate (Tetrahedron Letters, 1979, 399), Jones reagent (J. Chem. Soc. 1953, 2555) or platinum/oxygen (Adv. in Carbohydrate Chem. 17, 169 (1962)) or Collins oxidation and then Jones oxidation, can be used.

The oxidation with pyridinium chromate is performed at temperatures of 0° C. to 100° C., preferably 20° C. to 40° C. in a solvent inert toward the oxidizing agent, for example, dimethylformamide.

The oxidation with Jones reagent is performed at temperatures of −40° C. to +40° C., preferably −30° C. to 0° C. in acetone as a solvent.

The oxidation with platinum/oxygen is performed at temperatures of 0° C. to 60° C., preferably 20° C. to 40° C. in a solvent inert toward the oxidizing agent, such as, e.g., ethyl acetate.

The saponification of the esters of formula I is performed according to the methods known to one skilled in the art, such as, for example, with basic catalysts. The compounds of formula I can be separated by the usual separation methods into the optical isomers.

The release of the functionally modified hydroxy groups takes place according to known methods. For example, the cleavage of hydroxy protecting groups is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible inert organic solvent is suitably added. Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protecting groups takes place, for example, with tetrabutylammonium fluoride or with potassium fluoride in the presence of a crown ether. As a solvent, for example, tetrahydrofuran, diethyl ether, dioxane, methylene chloride, etc., are suitable. The cleavage is performed preferably at temperatures between 0° C. and 80° C.

The saponification of the acyl groups takes place, for example, with alkali or alkaline-earth carbonates or hydroxides in an alcohol or in the aqueous solution of an alcohol. As an alcohol, aliphatic alcohols are suitable, such as, e.g., methanol, ethanol, butanol, etc., preferably methanol. As alkali carbonates and hydroxides, potassium salts and sodium salts can be mentioned. The potassium salts are preferred.

As alkaline-earth carbonates and hydroxides, for example, calcium carbonate, calcium hydroxide and barium carbonate are suitable. The reaction takes place at −10° C. to +70° C. preferably at +25° C.

The leukotriene-B$_4$ derivatives of formula I with R$_2$ meaning a hydrogen atom can be converted to a salt with suitable amounts of the corresponding inorganic bases with neutralization. For example, during dissolving of the corresponding acids in water, which contains the stoichiometric amount of the base, the solid inorganic salt is obtained after evaporation of the water or after addition of a water-miscible solvent, e.g., alcohol or acetone.

For the production of an amine salt, the LTB$_4$ acid, e.g., is dissolved in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

If the initial product contains OH groups in the leukotriene-B$_4$ radical, these OH groups are also reacted. If finally end products are desired which contain free hydroxyl groups, a start is suitably made from initial products in which the latter are intermediately protected by preferably easily cleavable ether or acyl radicals.

The substitution of the chemically and metabolically labile cis- $\Delta^{6,7}$-double bond and the trans-$\Delta^{8,9}$-double bond of the LTB$_4$ by a 1,3-substituted phenyl ring or a 2,6-substituted pyridyl ring results in more stable leukotrienes with a phenyl or pyridyl ring in 6,9-position. Depending on the meaning of individual radicals R$_1$, B, A, D and the derivatizing of the functional groups, the compounds of general formula I are either a) chemically stable LTB$_4$ agonists or
b) chemically stable LTB$_4$ antagonists.

With the compounds of formula I, which represent receptor agonists, the activation of components of the immunological system imparted and stimulated by the LTB$_4$ receptor can be used therapeutically with various indications, such as infectious diseases, mycoses, burn injuries, in the treatment of tumors or, e.g., in the treatment of AIDS. In AIDS patients, e.g., a reduced release of LTB$_4$ in the stimulation of neutrophils has been reported.

The compounds of formula I, which represent receptor antagonists, act in an antiinflammatory and antiallergic manner. Consequently, the new leukotriene-B$_4$ derivatives of formula I represent valuable pharmaceutical active ingredients. The compounds of formula I are especially suitable for topical administration, since they exhibit a dissociation between desired topical effectiveness and undesirable systemic side effects.

These new leukotriene-B$_4$ derivatives of formula I are suitable in combination with the auxiliary agents and vehicles usual in galenic pharmaceutics for topical treatment of contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

The new leukotriene-B$_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat allergic diseases of the intestinal tract, such as colitis ulcerosa and colitis granulomatosa.

Further, the new compounds optionally in combination with the usual auxiliary agents and vehicles are also well-suited for the production of inhalants, which can be used to treat allergic diseases of the respiratory system, such as, for example, bronchial asthma or rhinitis.

The new leukotriene-B$_4$ derivatives, which represent LTB$_4$ antagonists, can also be used in combination with, e.g., lipoxygenase inhibitors, cyclooxygenase inhibitors, prostacyclin agonists, thromboxane antagonists, leukotriene-D$_4$ antagonists, leukotriene-E$_4$ antagonists, leukotriene-F$_4$ antagonists, phosphodiesterase inhibitors, or PAF antagonists.

The production of the pharmaceutical agent specialties takes place in the usual way, by the active ingredients being converted with suitable additives to the desired form of administration, such as, for example: solutions, lotions, ointments, creams or plasters. In the thus formulated pharmaceutical agents, the active ingredient concentration depends on the form of administration. In lotions and ointments, an active ingredient concentration of 0.0001% to 1% is preferably used.

The following embodiments are used to explain the process according to the invention.

EXAMPLE 1

(5RS)-5-Hydroxy-5-{6-[(1E)-(3RS)-3-hydroxy-1-undecenyl]-2-pyridyl}-pentanoic acid methyl ester A. A solution of 516 mg of 2,6-dibromopyridine in 4 ml of dimethylformamide is mixed with 1 g of (1E)-1-(tri-n-butylstannyl)-1-undecen-(3RS)-3-ol and 81 mg of 1,1′-bis-diphenylphosphino)-ferrocene-palladium(II) chloride and stirred under argon atmosphere for 24 hours at room temperature. The reaction mixture is poured into 20 ml of 5% hydrochloric acid, shaken out with diethyl ether, the organic phase is dried with sodium sulfate and concentrated by evaporation. The residue is chromatographed on silica gel with hexane/ethyl acetate/triethylamine 95/5/1. 355 mg of 2-bromo-6-[(1E)-(3RS)-3-hydroxy-1-undecenyl]-pyridine is thus obtained as colorless oil.

IR (CHCl$_3$): 2925, 2860, 1655, 1575, 1548, 1432, 1120, 985 cm$^{-1}$.

The organotin compound used in example 1A is described in German patent application P 3909326.3.

B. A solution of 326 mg of 2-bromo-6-[(1E)-(3RS)-3-hydroxy-1-undecenyl]-pyridine in 5 ml of tetrahydrofuran is mixed with 1.25 ml of n-butyllithium (1.6 molar in hexane) at $-78°$ C. with stirring and under argon atmosphere. After 10 minutes, a solution of 5-oxo-pentanoic acid methyl ester in 1 ml of tetrahydrofuran is added at $-78°$ C. and stirred for 2 hours at this temperature. The reaction mixture is mixed with water, shaken out with dichloromethane, dried on sodium sulfate, concentrated by evaporation and the crude product is chromatographed on silica gel with hexane/ethyl acetate 98/2. 188 mg of the title compound is thus obtained as colorless oil.

IR (CHCl$_3$): 3600, 2925, 2860, 1730, 1574, 1455, 1260, 1010 cm$^{-1}$.

EXAMPLE 2

(5RS)-5-Hydroxy-5-{6-[(1E)-(3RS)-3-hydroxy-1-undecenyl]-2-pyridyl}-pentanoic acid A solution of 140 mg of (5RS)-5-hydroxy-5-{6-[(1E)-(3RS)-3-hydroxy-1-undecenyl]-2-pyridyl)-pentanoic acid methyl ester in 6 ml of methanol is mixed with 6 ml of 0.5 n sodium hydroxide solution and stirred for 2 hours at room temperature. The methanol is removed in a vacuum, the residue is acidified to pH 4 with 0.5 n sulfuric acid, shaken out with ethyl acetate, the organic phase is dried on sodium sulfate and concentrated by evaporation. 125 mg of the title compound is thus obtained as colorless oil.

IR: 3370, 2960, 2922, 2852, 1710, 1570, 1455, 1260, 1080, 1020, 800 cm$^{-1}$.

EXAMPLE 3

2-[(1RS)-1-Hydroxy-1-(3-methoxycarbonylphenyl)-methyl]-6-[(1E)-(3RS)-3-hydroxy-1-undecenyl]-pyridine Under the conditions of example 1B, 326 mg of 2-bromo-6-[(1E)-(3RS)-3-hydroxy-1-undecenyl]-pyridine is reacted with 1.38 ml of n-butyllithium (1.6 molar in hexane) and 181 mg of 3-formylbenzoic acid methyl ester (J. Org. Chem. 31, 1966, 2585), worked up and chromatographed on silica gel with hexane/ethyl acetate 8/2. 105 mg of the title compound is obtained as colorless oil.

IR: 2030, 2860, 1720, 1290, 1095 cm$^{-1}$.

EXAMPLE 4

2-[(1RS)-1-Hydroxy-1-(3-carboxyphenyl)-methyl]-6-[(1E)-(3RS)-3-hydroxy-1-undecenyl]-pyridine Under the conditions of example 2, 80 mg of 2-[(1RS)-1-hydroxy-1-(3-methoxycarbonylphenyl)-methyl]-6-[(1E)-(3RS)-3-hydroxy-1-undecenyl]-pyridine in 4 ml of methanol is saponified with 4 ml of 0.5 n sodium hydroxide solution and worked up. 40 mg of the title compound is obtained as colorless foam.

IR: 3400, 2925, 2855, 1695, 1570, 1455, 1262, 970, 750 cm$^{-1}$.

EXAMPLE 5

3-{6-[(1E)-(3RS)-3-Hydroxy-1-undecenyl]-2-pyridyloxy}-benzoic acid methyl ester

A. A solution of 2.37 g of 2,6-dibromopyridine and 1.52 g of 3-hydroxybenzoic acid methyl ester in 10 ml of dimethylformamide is mixed with 6.6 g of cesium carbonate and heated to 120° C. with stirring for 3 hours. The reaction mixture is filtered on diatomaceous earth, rewashed with dichloromethane and the filtrate is concentrated by evaporation in a vacuum. The residue is distilled on a bulb tube at 140°-150° C. and 0.04 mbar. 2.98 g of 3-(6-bromo-2-pyridyloxy)-benzoic acid methyl ester of melting point 68°-69° C. is obtained.

IR (CHCl$_3$): 2925, 1720, 1580, 1560, 1420, 1285, 1100 cm$^{-1}$.

B. A solution of 617 mg of 3-(6-bromo-2-pyridyloxy)-benzoic acid methyl ester in 4 ml of dimethylformamide is mixed with 1.09 g of (1E)-1-(tri-n-butylstannyl)-1-undecen-(3RS)-3-ol and 74 mg of 1,1'-bis-(diphenylphosphino)-ferrocene-palladium(II) chloride and stirred under argon atmosphere for 48 hours at room temperature. The reaction mixture is chromatographed on silica gel with hexane/ethyl acetate=9/1. 340 mg of crude product is obtained as yellow oil, which is subjected to complete purification of the high-pressure liquid chromatography on silanized silica gel (RP 18 material) with methanol/water=9/1. 160 mg of the title compound is thus obtained as colorless oil.

IR (CHCl$_3$): 3605, 2930, 1722, 1590, 1570, 1435, 1260, 1100, 1015 cm$^{-1}$. EXAMPLE 6

3-{6-[(1E)-(3RS)-3-Hydroxy-1-undecenyl]-2-pyridyloxy}-benzoic acid

Under the conditions of example 2, 40 mg of 3-{6-[(1E)-(3RS)-3-hydroxy-1-undecenyl]-2-pyridyloxy)-benzoic acid methyl ester in 1 ml of methanol is saponified with 1 ml of 1 n sodium hydroxide solution and worked up. 29 mg of the title compound of melting point 85°-87° C. is obtained.

IR (CHCl$_3$): 2930, 1710, 1590, 1570, 1434, 1260, 1095, 1012 cm$^{-1}$.

EXAMPLE 7

4-{6-[(1E)-(7RS)-3-Hydroxy-1-undecenyl]-2-pyridylcarboylamino}-butyric acid ethyl ester A. 4 g of 6-bromopyridine-2-carboxylic acid and 25 g of thionyl chloride are refluxed for 1 hour. The excess thionyl chloride is removed in a vacuum and the residue is distilled on a bulb tube at 110° C. and 0.04 mbar. The 6-bromopyridine-2carboxylic acid chloride thus obtained is dissolved together with 3.32 g of 4-aminobutyric acid ethyl ester, hydrochloride in 40 ml of dioxane, mixed under ice cooling with 6 g of triethylamine and stirred for 5 hours at room temperature. The reaction mixture is added to water, extracted with diethyl ether, dried (sodium sulfate) and concentrated by evaporation. The residue is distilled on a bulb tube at 170° C. and 0.04 mbar and 3.2 g of 4-(6-bromo-2-pyridylcarbonylamino)-butyric acid ethyl ester is thus obtained as bright yellow oil.

IR (CHCl$_{13}$): 3400, 2930, 1720, 1675, 1520, 1425, 1300 cm$^{-1}$.

B. Under the conditions of example 5B, 6.30 mg of 4-(6-bromo-2-pyridylcarbonylamino)-butyric acid ethyl ester and 1.007 g of (1E)-1-(tri-n-butylstannyl)-1-undecen-(3RS)-3-ol in 4 ml of dimethylformamide are reacted in the presence of 71 mg of 1,1'-bis-(diphenylphosphino)-ferrocene-palladium(II) chloride as catalyst and the reaction mixture is chromatographed on silica gel with hexane/ethyl acetate=95/5 to 8/2. 300 mg of the title compound is obtained as colorless oil.

IR (CHCl$_3$): 3390, 2925, 2860, 1725, 1670, 1525, 1450, 1260 cm$^{-1}$.

EXAMPLE 8

4-{6-[(1E)-(3RS)-3-Hydroxy-1-undecenyl]-2-pyridylcarbonylamino}-butyric acid

Under the conditions of example 2, 60 mg of 4-{6-[(1E)-(3RS)-3-hydroxy-1-undecenyl]-2-pyridylcarbonylamino}-butyric acid ethyl ester in 1.5 ml of methanol is saponified with 1.5 ml of 1 n sodium hydroxide solution and worked up. 35 mg of the title compound is obtained as colorless oil.

IR (CHCl$_{13}$): 3390, 2925, 2860, 1722, 1670, 1525, 1450, 1260 cm$^{-1}$.

EXAMPLE 9

5-{6-[(1E)-(3RS)-3-Hydroxy-1-undecenyl]-2-pyridylamino}-5-oxo-pentanoic acid methyl ester A. A solution of 1.0 g of 2-amino-6-bromopyridine and 580 mg of triethylamine in 12 ml of tetrahydrofuran is mixed with stirring and ice cooling by instillation with 0.78 ml of glutaric acid methyl ester chloride and the mixture is stirred for 17 hours at room temperature. The reaction mixture is added to water, shaken out with diethyl ether, the organic phase is dried (sodium sulfate) and concentrated by evaporation. The residue is chromatographed on silica gel with dichloromethane/methanol=95/5. 668 mg of 5-(6-bromo-2-pyridylamino)-5-oxo-pentanoic acid methyl ester of melting point 128°-131° C. is obtained.

B. Under the conditions of example 5B, 603 mg of 5-(6-bromo-2-pyridylamino)-5-oxo-pentanoic acid methyl ester and 1.01 g of (1E)-1-(tri-n-butylstannyl)-1-undecen-(3RS)-3-ol in 12 ml of dimethylformamide are reacted in the presence of 71 mg of 1,1'-bis-(diphenylphosphino)-ferrocene-palladium(II) chloride as catalyst and the reaction mixture is chromatographed on silica gel with hexane/ethyl acetate=95/5 to 75/25. 155 mg of the title compound is obtained as colorless oil.

IR (CHCl$_3$): 3420, 2925, 2860, 1730, 1695, 1575, 1450, 1260, 1095, 1010 cm$^{-1}$.

EXAMPLE 10

4-{6-[(1E)-(3RS)-3-Hydroxy-1-undecenyl]-2-pyridylamino}-5-oxo-pentanoic acid

Under the conditions of example 2, 60 mg of 4-{6-[(1E)-(3RS)-3-hydroxy-1-undecenyl]-2-pyridylamino}-5-oxo-pentanoic acid methyl ester in 1.5 ml of methanol is saponified with 1.5 ml of 1 n sodium hydroxide solution and worked up. 40 mg of the title compound is obtained as colorless oil.

IR (CHCl$_3$): 2935, 2865, 1700, 1580, 1458 cm$^{-1}$.

EXAMPLE 11

4-{6-[(1E)-(3RS)-3-Hydroxy-1-undecenyl]-2-pyridyloxy}-acetic acid methyl ester

A. A suspension of 178 mg of sodium hydride (80% dispersion in mineral oil) in 4 ml of dimethylformamide is mixed under argon atmosphere, stirring and ice cooling with a solution of 361 mg of glycolic acid methyl ester in 2 ml of dimethylformamide and stirred for 3 hours at room temperature. Then, a solution of 948 mg of 2,6-dibromopyridine in 2 ml of dimethylformamide is added under ice cooling and the mixture is stirred for 48 hours at room temperature. The reaction mixture is poured on ice and extracted with ethyl acetate. The organic phase is washed 4 times with saturated common salt solution, dried on sodium sulfate and concentrated by evaporation. 790 mg of 2-(6-bromo-2-pyridyloxy)-acetic acid methyl ester is obtained as oily crude product.

B. Under the conditions of example 5B, 780 mg of the above-named crude product and 1.95 g of (1E)-1-(tri-n-butylstannyl)-1-undecen-(3RS)-3-ol in 23 ml of dimethylformamide are reacted in the presence of 138 mg of 1,1'-bis-(diphenylphosphino)-ferrocene-palladium(II) chloride as catalyst. The reaction mixture is poured on ice, shaken out with ethyl acetate, the organic phase is washed 4 times with saturated common salt solution, dried on sodium sulfate and concentrated by evaporation. The residue is chromatographed on silica gel with hexane/ethyl acetate=95/5. 161 mg of the title compound is obtained as colorless oil.

IR (CHCl$_3$): 2960, 2930, 2580, 1753, 1590, 1575, 1448, 1260 cm$^{-1}$.

EXAMPLE 12

2-{6-[(1E)-(3RS)-3-Hydroxy-1-undecenyl]-2-pyridyloxy)-acetic acid

Under the conditions of example 2, 25 mg of 2-{6-[(1E)-(3RS)-3-hydroxy-1-undecenyl]-2-pyridyloxy)-acetic acid methyl ester in 1.5 ml of methanol is saponified with 1.5 ml of 1 n sodium hydroxide solution and worked up. 20 mg of the title compound is obtained as bright yellow oil.

IR (CHCl$_{13}$): 2960, 2930, 2857, 1735, 1588, 1574, 1448, 1260 cm$^{-1}$.

EXAMPLE 13

2-(3-Methoxycarbonylbenzoyl)-6-[(1E)-(3RS)-3-hydroxy-1-undecenyl]-pyridine

Under the conditions of example 1B, 652 mg of 2-bromo-6-[(1E)-(3RS)-3-hydroxy-1-undecenyl]-pyridine in 3 ml of tetrahydrofuran is mixed with 2.75 ml of n-butyllithium (1.6 molar in hexane) and 427 mg of isophthalic acid dimethyl ester in 3 ml of tetrahydrofuran, worked up and chromatographed on silica gel with hexane/ethyl acetate=95/5 to 75/25. 130 mg of an oily crude product is obtained, which is subjected to complete purification of the high-pressure liquid chromatography on silanized silica gel (RP18 material) with methanol/H$_2$O=85/15. 58 mg of the title compound is thus obtained as colorless oil.

IR: 2928, 2858, 1728, 1668, 1580, 1440, 1272, 1235, 1162, 740, 725 cm$^{-1}$.

EXAMPLE 14

2-(3-Carboxybenzoyl)-6-[(1E)-(3RS)-3-hydroxy-1-undecenyl]-pyridine

Under the conditions of example 2, 20 mg of 2-(3-methoxycarbonylbezoyl)-6-[(1E)-(3RS)-3-hydroxy-1-undecenyl]-pyridine in 1 ml of methanol is saponified with 2 ml of 1 n sodium hydroxide solution and worked up. 15 mg of the title compound is obtained as colorless oil.

IR (CHCl$_3$): 3018, 2963, 2930, 1720, 1670, 1607, 1265, 1100, 1015 cm$^{-1}$.

EXAMPLE 15

2-[3,5-bis-(Methoxycarbonyl)-benzoyl]-6-[(1E)-(3RS)-3-hydroxy-1-undecenyl]-pyridine Under the conditions of example 1B, 1 g of 2-bromo-6-[(1E)(3RS)-3-hydroxy-1-undecenyl)-pyridine in 10 ml of tetrahydrofuran is mixed with 4.26 ml of n-butyllithium (1.6 molar in hexane) and 807 mg of 1,3,5-benzenetricarboxylic acid trimethylester in 6 ml of tetrahydrofuran, worked up and chromatographed on silica gel with hexane/ethyl acetate=95/5 to 75/25. 203 mg of oily crude product is obtained, which is subjected to complete purification of the high-pressure liquid chromatography on silanized silica gel (RP 18 material) with methanol/H$_2$O=9:1. 74 mg of the title compound is thus obtained as colorless oil.

IR (Film): 3560-3160, 2920, 2850, 1730, 1670, 1590, 1450, 1345, 875, 850, 820 cm$^{-1}$.

EXAMPLE 16

2-[3,5-bis-(Carboxy)-benzoyl]-6-[(1E)-(3RS)-3-hydroxy-1-undecenyl]-pyridine

Under the conditions of example 2, 20 mg of 2-[3,5-bis-(methoxycarboyl)-benzoyl]-6-[(1E)-(3RS)-3-hydroxy-1-undecenyl]-pyridine in 2 ml of methanol is saponified with 2 ml of 1 n sodium hydroxide solution and worked up. 6 mg of the title compound is obtained as colorless oil.

IR (CHCl$_3$): 3580-3260, 3005, 1725, 1608, 1052, 1030, 1012, 930 cm$^{-1}$.

EXAMPLE 17

(5RS)-5-Hydroxy-5-{6-[(1E, 3E)-(5RS)-5-hydroxy-1,3-tridecadienyl]-2-pyridyl}-pentanoic acid methyl ester A. A solution of 5.88 g of 4-phosphonocrotonic acid triethyl ester in 60 ml of tetrahydrofuran is mixed in portions with 2.5 g of potassium-tert-butanolate with stirring and under argon atmosphere at −20° C. After 30 minutes, a solution of 2.6 g of 6-bromopyridine-2-aldehyde is instilled at −20° C. and the mixture is stirred at this temperature for another hour. The reaction mixture is poured on ice, shaken out with diethyl ether, the organic phase is washed with saturated common salt solution, dried on sodium sulfate and concentrated by evaporation. The residue is chromatographed on silica gel with hexane/ethyl acetate=95/5. 2.66 g of 5-(6-bromo-2-pyridyl)-(E,E)-2,4-pentadienoic acid ethyl ester is obtained as crude product.

B. A solution of 2.6 g of 5-(6-bromo-2-pyridyl)-(E,E)-2,4-pentadienoic acid ethyl ester in 73 ml of toluene is mixed with stirring and under argon atmosphere at −70° C. by instillation with 15.4 ml of diisobutylaluminum hydride (20% solution in toluene) and the mixture is stirred for 45 more minutes at this temperature. The reaction mixture is mixed at −70° C. in succession by instillation with 5.5 ml of isopropanol and 7.3 ml of water, stirred for 1 hour at room temperature, suctioned off on diatomaceous earth, rewashed with dichloromethane, the filtrate is dried on sodium sulfate and concentrated by evaporation. 2.2 g of 5-(6-bromo-2-pyridyl)-(E,E)-2,4-pentadien1-ol is obtained as crude product.

C. A solution of 2 g of 5-(6-bromo-2-pyridyl)-penta-(E,E)2,4-dien-1-ol in 32 ml of dichloromethane is vigorously stirred with 5.8 g of manganese oxide for 2 hours. The reaction mixture is suctioned off on diatomaceous earth, concentrated by evaporation and the residue is chromatographed on silica gel with dichloromethane. 1.17 g of 5-(6-bromo-2-pyridyl)-(E,E)-2,4-pentadienaldehyde is obtained as crude product.

D. A solution of octylmagnesium bromide (produced from 150 mg of magnesium in 5 ml of diethyl ether and 1.14 g of octyl bromide in 2.5 ml of diethyl ether) is instilled in a solution of 1.17 g of 5-(6-bromo-2-pyridyl)-(E,E)-2,4-pentadienaldehyde in 25 ml of diethyl ether with stirring and under argon atmosphere at −20° C. After 1.5 hours at −20° C., the reaction mixture is mixed with 15 ml of saturated ammonium chloride solution, shaken out with diethyl ether, dried on sodium sulfate, concentrated by evaporation and the residue is chromatographed on silica gel with hexane/ethyl acetate=95/5. 477 mg of 2-bromo-6-[(1E,3E)-(5RS)-5-hydroxy-1,3-tridecadienyl]-pyridine is obtained as crude product.

E. Under the conditions of example 1B, 470 mg of 2-bromo-6-[(1E, 3E)-(5RS)-5-hydroxy-1,3-tridecadienyl]-pyridine in 7 ml of tetrahydrofuran is mixed with 1.84 ml of n-butyllithium (1.6 molar in hexane) and 200 mg of 5-oxo-pentanoic acid methyl ester in 1.5 ml of tetrahydrofuran, worked up and chromatographed on silica gel with hexane/ethyl acetate=95/5. 29 mg of the title compound is obtained as colorless oil.

IR (CHCl$_{13}$): 3615, 2930, 1730, 1570, 1452, 1390, 1040, 875 cm$^{-1}$.

EXAMPLE 18

(5RS)-5-Hydroxy-5-{3-[(1E,3E)-(5RS)-5-hydroxy-1,3-tridecadienyl]-phenyl}-pentanoic acid 914 mg of tetrabutylammonium fluoride is added to a solution of 500 mg of (5RS)-5-acetoxy-5-{3-[(1E,3E)-(5RS)-5-acetoxy-1,3-tridecadienyl]-phenyl}-pentan-1-ol-tert-butyldimethylsilylether in 28 ml of tetrahydrofuran at 0° C., stirred for 30 minutes at 0° C. and for 4.5 hours at 24° C. Then, it is diluted with ether, washed with brine, dried on sodium sulfate and concentrated by evaporation in a vacuum. The residue is chromatographed on silica gel. With hexane/0–20% ethyl acetate, 193 mg of (5RS)-5-acetoxy-5-{3-{(1E,3E)-(5RS)-5-acetoxy-1,3-tridecadienyl}-phenyl}-pentan-1-ol is obtained as colorless oil.

IR (CHCl$_3$): 3620, 3480, 2960, 2930, 2860, 1730, 1372, 1245, 1022, 990 cm$^{-1}$.

A solution of 193 mg of the above-produced alcohol in 5 ml of methylene chloride is instilled in a mixture of 1.25 g of Collins reagent (chromic acid-pyridine complex) in 20 ml of methylene chloride at 0° C. with stirring, and it is stirred for 1 hour at 0° C. Then, enough Celite is added until a thick paste results, the latter is suspended with hexane/ethyl acetate (1:1), filtered off, washed well with hexane/ethyl acetate (1:1) and the filtrate is concentrated by evaporation in a vacuum. 150 mg of (5RS)-5-acetoxy-5-{3-[(1E,3E)-(5RS)-5-acetoxy-1,3-tridecadienyl]-phenyl)-pentanal is obtained as colorless oil.

IR (CHCl$_3$): 3020, 2960, 2930, 2860, 2730, 1730, 1375, 1245, 1022, 990 cm$^{-1}$.

0.3 ml of Jones reagent (J. Chem. Soc. 1953, 2555) is instilled in a solution of 150 mg of the above-produced aldehyde in 11 ml of acetone with stirring at −30° C. and stirred for one hour at −30° C. Then, 0.23 ml of isopropanol is added, stirred for 15 minutes, diluted with ether, filtered, washed neutral with brine, dried on magnesium sulfate and concentrated by evaporation in a vacuum. The residue is chromatographed on silica gel. With hexane/0–50% ethyl acetate, 52 mg of (5RS)-5-acetoxy-5-{3-[(1E,3E)-(5RS)-5-acetoxy-1,3-tridecadienyl]-phenyl)-pentanoic acid is obtained as colorless oil.

IR (CHCl$_3$): 3520, 3200, 2960, 2930, 2860, 1730, 1372, 1245, 1020, 990 cm$^{-1}$.

0.77 mil of 0.5 n sodium hydroxide solution is added to a solution of 34 mg of the above-produced acid in 0.62 ml of methanol at 0° C. and stirred for 1.8 hours at 24° C. Then, it is diluted with 2.5 ml of water and acidified to pH 6 at 0° C. with 0.5 n of sulfuric acid. It is extracted three times with ethyl acetate, the organic phase is shaken with a little water, dried on sodium sulfate and concentrated by evaporation in a vacuum. The residue is chromatographed on silica gel. With hexane/30–85% ethyl acetate, 15 mg of the title compound is obtained as colorless oil.

IR (Film): 3420, 2960, 2930, 2860, 1723, 1380, 1070, 990 cm$^{-1}$.

The initial material for the above-named title compound is produced as follows:

A. 5-[3-(tert-Butyldimethylsilyloxymethyl)-phenyl]-(2E,4E)-pentadienoic acid ethyl ester 33.3 g of tert-butyldimethylsilyl chloride is added to a solution of 30 g of 3-hydroxymethylbenzyl alcohol and 30 g of imidazole in 250 ml of dimethylformamide at 0° C. under argon and stirred for 20 hours at 25° C. It is diluted with 1.5 l of ether, shaken twice with 100 ml of 10% sulfuric acid each, washed neutral with brine, dried on sodium sulfate and concentrated by evaporation in a vacuum. The residue is chromatographed on silica gel. With hexane/0–80% ether, 23.4 g of 3-tert-butyldimethylsilyloxymethyl-benzyl alcohol is obtained as colorless oil.

IR (CHCl$_3$): 3680, 3610, 3440, 2960, 2930, 2860, 1470, 1255, 840 cm$^{-1}$.

A solution of 21 g of the above-produced silyl ether in 320 ml of methylene chloride is mixed with 82 g of manganese dioxide and stirred for 8 hours at 25° C. Then, it is filtered and concentrated by evaporation. 20.7 g of 3-tert-butyldimethylsilyloxymethyl-benzaldehyde is obtained as colorless oil.

IR (CHCl$_3$): 2960, 2935, 2860, 1700, 1610, 1590, 1470, 1255, 840 cm$^{-1}$.

For Wittig-Horner olefination, 14 g of potassium-tert-butylate is added at −20° C. to a solution of 33.4 g of phosphonocrotonic acid triethyl ester in 340 ml of tetrahydrofuran and stirred for 30 minutes at −20° C. Then, a solution of 20 g of 3-tertbutyldimethylsilyloxymethyl-benzaldehyde in 180 ml of tetrahydrofuran is instilled in this solution and stirred for 1 hour at −20° C. It is then poured on 700 ml of ice water, extracted three times with 500 ml of ether each, the organic phase is washed neutral with brine, dried on sodium sulfate and concentrated by evaporation in a vacuum. The residue thus obtained is chromatographed on silica gel. With hexane/0–30% ether, 25.8 g of the title compound is obtained as colorless oil.

IR (CHCl$_3$): 2960, 2935, 2860, 1705, 1627, 1470, 1370, 1245, 998, 840 cm$^{-1}$.

B. 5-[3-(tert-Butyl-dimethylsilyloxymethyl)-phenyl]-(2E,4E)-pentadienal 56 ml of an approximately 1.2 molar solution of diisobutylaluminum hydride in toluene is instilled in a solution of 10.6 g of the ester, produced according to example 1A, in 250 ml of toluene at −70° C. under argon and stirred for one hour at −70° C. Then, 10 ml of isopropanol followed by 25 ml of water is instilled and stirred for 2 hours at 22° C., filtered, washed with toluene and concentrated by evaporation in a vacuum. 10.6 g of 5-[3-(tert-butyldimethylsilyloxymethyl)-phenyl]-(2E,4E)-pentadien-1-ol is obtained as colorless oil.

IR (CHCl$_3$): 3610, 3450, 3005, 2960, 2935, 2860, 1470, 1380, 1255, 990, 840 cm$^{-1}$.

A solution of 10.6 g of the above-produced alcohol in 600 ml of methylene chloride is mixed with 38 g of manganese dioxide and stirred for 4 hours at 25° C. Then, it is filtered and concentrated by evaporation. 7.8 g of the title compound is obtained as colorless oil.

IR (CHCl$_3$): 3605, 2960, 2935, 2860, 1675, 1622, 1470, 1245, 988, 840 cm$^{-1}$.

C. 5-Acetoxy-1-[3-(tert-butyldimethylsilyloxymethyl)-phenyl]-(1E,3E)-tridecadiene A solution of 7.96 ml of n-octyl bromide in 12 ml of ether is instilled in 1.12 g of magnesium in 5 ml of ether with heating and stirred for 30 minutes at 25° C. A solution of 7.8 g of the aldehyde, produced according to B, in 150 ml of ether, is instilled in 17 ml of this Grignard solution at −20° C. under argon and stirred for 2 hours at −20° C. It is mixed with 100 ml of saturated ammonium chloride solution, extracted three times with ether, the organic phase is shaken with brine, dried on magnesium sulfate and concentrated by evaporation in a vacuum. 11 g of 5-hydroxy-1-[3-(tert-butyldimethyl-silyloxymethyl)-phenyl]-(1E,3E)-tridecadiene is obtained as colorless oil.

IR (CHCl$_3$): 3610, 3460, 3000, 2960, 2930, 2860, 1470, 1255, 988, 840 cm$^{-1}$.

For acetylation, 31 ml of acetic anhydride is added to a solution of 11 g of the above-produced alcohol in 120 ml of pyridine and stirred for 15 hours at 23° C. Then, it is concentrated by evaporation in a vacuum with adding toluene and the residue is chromatographed on silica gel. With hexane/0–3% ethyl acetate, 8.9 g of the title compound is obtained as colorless oil.

IR (CHCl$_3$): 2960, 2937, 2860, 1730, 1470, 1372, 1255, 990, 840 cm$^{-1}$.

D. (5RS)-5-Acetoxy-5-{3[(1E,3E)-(5RS)-5-acetoxy-1,3-tridecadienyl-]-phenyl}-pentan-1-ol-tert-butyldimethylsilylether 4.9 g of tetrabutylammonium fluoride is added to a solution of 2.4 g of the acetate, produced according to C, in 150 ml of tetrahydrofuran at 0° C. and stirred for 1.5 hours at 24° C. Then, it is diluted with 250 ml of ether, shaken with brine, dried on sodium sulfate and concentrated by evaporation in a vacuum. The obtained residue is chromatographed on silica gel. With hexane/0–25% ethyl acetate, 1.5 g of 3-[(1E,3E)-5-acetoxy-1,3-tridecadienyl]-benzyl alcohol is obtained as colorless oil.

IR (CHCl$_3$): 3610, 3440, 3005, 2960, 2930, 2860, 1730, 1375, 1250, 990 cm$^{-1}$.

11 g of manganese dioxide is added to a solution of 1.5 g of the above-produced benzyl alcohol in 30 ml of methylene chloride and stirred for 3 hours at 24° C. Then, it is filtered, washed with methylene chloride and concentrated by evaporation in a vacuum. 1.3 g of 3-[(1E,3E)-5-acetoxy-1,3-tridecadienyl]-benzaldehyde is obtained as colorless oil.

IR (CHCl$_3$): 3020, 2960, 2930, 2860, 2740, 1727, 1695, 1600, 1372, 1245, 988 cm$^{-1}$.

A solution of 6.7 g of 4-chloro-1-tert-butyldimethylsilyloxybutane in 6 ml of tetrahydrofuran and 0,187 ml of dibromoethane is instilled in 1.4 g of magnesium at 25° C. under argon, heated for 5 minutes to 70° C., stirred for 30 minutes at 25° C. and diluted with 18.8 ml of tetrahydrofuran.

A solution of 1.3 g of 3-[(1E,3E)-5-acetoxy-1,3-tridecadienyl]-benzaldehyde in 16 ml of tetrahydrofuran is instilled in 16 ml of this magnesium-organic solution at −70° C. under argon and stirred for 1.5 hours at −70° C. It is mixed with 150 ml of saturated ammonium chloride solution, extracted three times with ether, the organic phase is shaken with brine, dried on magnesium sulfate and concentrated by evaporation in a vacuum. The residue is dissolved in 22 ml of pyridine, mixed with 12 ml of acetic anhydride and stirred for 16 hours at 22° C. Then, it is concentrated by evaporation in a vacuum with adding toluene and the residue is chromatographed on silica gel (flash chromatography). With hexane/0–3.5% ethyl acetate, 1.1 g of the title compound is obtained as colorless oil.

IR (CHCl$_3$): 3005, 2960, 2930, 2860, 1730, 1372, 1250, 1095, 988, 838 cm$^{-1}$.

EXAMPLE 19

(5RS)-5-Hydroxy-5-{3-[(1E)-(3RS)-3-hydroxy-1-undecenyl]-phenyl}-pentanoic acid 630 mg of pyridinium-p-toluenesulfonate is added to a solution of 630 mg of (5RS)-5-acetoxy-5-{3-[(1E)-(3RS)-3-diphenyl-tert-butylsilyloxy-1-undeceyl]-phenyl}-petan-1-ol-tert-butyldimethylsilylether in 12 ml of ethanol at 22° C. under argon and stirred for 3.5 hours at 22° C. Then, it is diluted with ether, washed with water, dried on sodium sulfate and concentrated by evaporation in a vacuum. The residue is chromatographed on silica gel. With hexane/0–20% ethyl acetate, 472 mg of (5RS)-5-acetoxy-5-{3-[(1E)-(3RS)-3-diphenyl-tert-butylsilyloxy-1-undecenyl]-phenyl}-pentan-1-ol is obtained as colorless oil.

IR (CHCl$_3$): 3620, 3450, 3000, 2960, 2930, 2860, 1730, 1375, 1245, 1110, 965, 700 cm$^{-1}$.

4 g of Collins reagent (chromic acid-pyridine complex) is added to a solution of 470 mg of the above-produced alcohol in 50 ml of methylene chloride at 0° C. under argon and stirred for 30 minutes at 0° C. Then, enough Celite is added until a thick paste results. The latter is suspended with hexane/ether (1+1), filtered off, washed well with hexane/ether (1+1) and the filtrate is concentrated by evaporation in a vacuum. 456 mg of (5RS)-5-acetoxy-5-{3-[(1E)-(3RS)-3-diphenyl-tert-butylsilyloxy-1-undecenyl]-phenyl)-pentanal is obtained as colorless oil.

IR (CHCl$_3$): 3000, 2960, 2930, 2860, 2730, 1728, 1372, 1245, 1110, 968, 700 cm$^{-1}$.

1 ml of Jones reagent (J. Chem. Soc. 1953, 2555) is instilled in a solution of 456 mg of the above-produced aldehyde in 20 ml of acetone with stirring at −30° C. and stirred for 35 minutes at −20° C. Then, 0.3 ml of isopropanol is added, stirred for 10 minutes at −20° C. diluted with ether, filtered, washed neutral with brine, dried on sodium sulfate and concentrated by evaporation in a vacuum. The residue is chromatographed on silica gel. With hexane/0–50% ethyl acetate, 397 mg of (5RS)-5-acetoxy-5-{3-[(1E)-(3RS)-3-diphenyl-tert-butylsilyloxy-1-undecenyl]-phenyl}-pentanoic acid is obtained as colorless oil.

IR (CHCl$_3$): 3520, 3180, 2950, 2930, 2860, 1730, 1375, 1245, 1110, 968, 700 cm$^{-1}$.

390 mg of tetrabutylammonium fluoride is added to a solution of 390 mg of the above-produced acid in 20 ml of tetrahydrofuran under argon at 24° C. and stirred for 6 hours at 24° C. Then, it is diluted with ether, the organic phase is shaken with brine, dried on sodium sulfate and concentrated by evaporation in a vacuum. The residue is chromatographed on silica gel. With hexane/10–70% ethyl acetate, 278 mg of (5RS)-5-acetoxy-5-{3-[(1E)-(3RS)-3-hydroxy-1-undecenyl]-phenyl)-pentanoic acid is obtained as colorless oil.

IR (CHCl$_3$): 3610, 3520, 3200, 3010, 2960, 2930, 2860, 1730, 1375, 1245, 970 cm$^{-1}$.

0.5 n sodium hydroxide solution is added to a solution of 90 mg of the above-produced acid at 22° C. and stirred for 2 hours at this temperature. Then, it is diluted with 5 ml of water and acidified to pH 5 at 0° C. with 10% sulfuric acid. It is extracted four times with ethyl acetate, the organic phase is shaken with brine, dried on sodium sulfate and concentrated by evaporation in a vacuum. The residue is chromatographed on silica gel. With hexane/30–90% ethyl acetate, 61 mg of the title compound is obtained as colorless oil.

IR (CHCl$_3$): 3610, 3410, 3160, 3005, 2960, 2930, 2860, 1730, 1240, 968 cm$^{-1}$.

The initial material for the above-named title compound is produced as follows:

A. 3-Diphenyl-tert-butylsilyloxy-1-[3-(tert-butyl-dimethylsilyloxymethyl)-phenyl]-(1E)-udecene For Wittig-Horner olefination, 3.64 g of potassium-tertbutylate is added at −20° C. to a solution of 9.41 g of 2-oxo-decyl-phosphonic acid dimethyl ester in 280 pf tetrahydrofuran and stirred for 20 minutes at this temperature. Then, a solution of 4.5 g of 3-tert-butyldimethylsilyloxymethylbenzaldehyde (see example 18A) in 150 ml of tetrahydrofuran is instilled in this solution and stirred for one hour at −20° C. It is poured on 500 ml of saturated ammonium chloride solution, extracted with ethyl acetate, the organic phase is washed neutral with brine, dried on sodium sulfate and concentrated by evaporation in a vacuum. The residue thus obtained is chromatographed on silica gel. With hexane/5–20% ethyl acetate, 6.5 g of 1-[3-(tert-butyldimethylsilyloxymethyl)-phenyl]-(1E)-udecen-3-one is obtained as colorless oil.

IR (CHCl$_3$): 3000, 2960, 2930, 1690, 1655, 1612, 1470, 1258, 970, 840 cm$^{-1}$.

483 mg of sodium borohydride is added to a solution of 6.5 g of the above-produced ketone in 270 ml of methanol under argon at 0° C. and stirred for one hour at this temperature. Then, it is mixed with 1.5 ml of glacial acetic acid, diluted with 150 ml of water and extracted three times with 200 ml of ethyl acetate each. The organic phase is washed neutral with brine, dried on magnesium sulfate and concentrated by evaporation in a vacuum. The residue is chromatographed on silica gel. With hexane/0–20% ethyl acetate, 5.65 g of 1-[3-(tert-butyldimethylsilyloxymethyl)phenyl]-(1E)-undecen-3-ol is obtained as colorless oil.

IR (CHCl$_3$): 3610, 3000, 2960, 2930, 2860, 1470, 1255, 968, 840 cm$^{-1}$.

3.6 g of imidazole and 6.18 g of tert-butyldiphenylsilyl chloride are added to a solution of 5.65 g of the above-produced alcohol in 100 ml of dimethylformamide at 0° C. under argon and stirred for 16 hours at 22° C. Then, it is added to water, extracted with hexane/ether (1+1), the organic phase is washed with water, dried on sodium sulfate and concentrated by evaporation in a vacuum. The residue is chromatographed on silica gel. With hexane/0–10% ethyl acetate, 5.1 g of the title compound is obtained as colorless oil.

IR (CHCl$_3$): 3005, 2960, 2930, 2860, 1470, 1255, 970, 840, 700 cm$^{-1}$.

B. (5RS)-5-{3-[(1E)-(3RS)-3-Diphenyl-tert-butylsilyloxy-1-undecenyl]-phenyl}-5-acetoxy-pentan-1-ol-tert-butyldimethylsilylether 50 ml of a mixture of acetic acid/water/tetrahydrofuran (65+35+10) is added to a solution of the silyl ether, produced according to example 19A, in 100 ml of tetrahydrofuran, and stirred for 8 hours at 50° C. and for 16 hours at 24° C. Then, it is concentrated by evaporation with adding toluene and 5.1 g of 3-[(1E)-3-diphenyl-tert-butylsilyloxy-1-undecenyl]-benzyl alcohol is obtained as colorless oil.

IR (CHCl$_3$): 3610, 3470, 3000, 2960, 2930, 2860, 1470, 1250, 970, 700 cm$^{-1}$.

6 g of manganese dioxide is added to a solution of 1.5 g of the above-produced alcohol in 20 ml of methylene chloride and stirred for 4 hours at 22° C. Then, it is filtered on-Celite, washed with methylene chloride and concentrated by evaporation in a vacuum. The residue is chromatographed on silica gel. With hexane/ethyl acetate (9+1), 1.47 g of 3-[(1E)-3-diphenyl-tert-butyl-silyloxy-1-undecenyl]-benzaldehyde is obtained as colorless oil.

IR (CHCl$_3$): 3000, 2960, 2930, 2860, 2740, 1700, 1605, 1112, 970, 705 cm$^{-1}$.

20 ml of a Grignard solution of 4-chloro-1-tert-butyldimethylsilyloxybutane and magnesium in tetrahydrofuran (see example 18D) is instilled in a solution of 1.47 g of the above-produced aldehyde in 10 ml of tetrahydrofuran under argon at −70° C. and stirred for 30 minutes. It is added on saturated ammonium chloride solution, extracted with ether, the organic phase is washed with water, dried on sodium sulfate and concentrated by evaporation in a vacuum. The residue is dissolved in 8 ml of pyridine, mixed with 2 ml of acetic anhydride and stirred for 20 hours at 24° C. Then, it is concentrated by evaporation in a vacuum with adding toluene and the residue is chromatographed on silica gel. With hexane/0–15% ethyl acetate, 630 mg of the title compound is obtained as colorless oil.

IR (CHCl$_3$): 3000, 2965, 2940, 2855, 1730, 1470, 1375, 1250, 1105, 968, 840, 700 cm$^{-1}$.

EXAMPLE 20

5-{6-[(1E)-(3RS)-3-Hydroxy-1-undecenyl]-2-pyridyl}-4-oxo-pentanoic acid methyl ester A. A solution of 4.73 g of 2,6-dibromopyridine in 150 ml of triethylamine is mixed under ice cooling with 2.69 g of pentanoic acid methyl ester, 350 mg of bis-triphenylphosphinepalladium(II) chloride and 48 mg of copper(I) iodide and the mixture is stirred for 1 hour. Then, the ice bath is removed and it is stirred for 3 hours at room temperature. The precipitate—consisting of 2,6-bis-(4-methoxycarbonyl-1-butinyl)-pyridine and triethylammonium bromide—is suctioned off and the filtrate is evaporated to dryness. The residue is chromatographed on silica gel with hexane/ethyl acetate=95/5 to 75/25. 2.32 g of 5-(6-bromo-2-pyridyl)-4-pentanoic acid methyl ester of melting point 59–61° C. is obtained.

IR (KBr): 3040, 2230, 1728, 1572, 1548, 1433, 1162, 800 cm$^{-1}$.

B. A mixture of 500 mg of red mercury oxide, 0.2 ml of boron trifluoride-diethyl ether complex and 10 mg of trichloroacetic acid in 1 ml of methanol is heated to 60° C. and a solution of 9.4 g of 5-(6-bromo-2-pyridyl)-4-pentanoic acid methyl ester in 15 ml of methanol is added to this catalyst solution at room temperature and the mixture is stirred for 2 hours at room temperature. Then, the reaction mixture is poured in 5% sulfuric acid, extracted with ethyl acetate, dried (Na$_2$SO$_4$) and concentrated by evaporation. 6.3 g of 5-(6-bromo-2-pyridyl)-4-oxo-pentanoic acid methyl ester is obtained as bright yellow oil.

IR: 2955, 1738, 1720, 1585, 1555, 1440, 1410, 1360, 1200, 1165, 1120, 988 cm$^{-1}$.

C. Under the conditions of example 5B, 1.3 g of 5-(6-bromo-2-pyridyl)-4-oxo-pentanoic acid methyl ester and 2.31 g of (1E)-1-tri-n-butylstannyl)-1-undecen-(3RS)-3-ol in 13 ml of dimethylformamide are reacted in the presence of 320 mg of 1,1'-bis(diphenylphosphino)-ferrocene-palladium(II) chloride as catalyst and worked up analogously to example 11B. The crude product is chromatographed on silica gel with hexane/ethyl acetate 95/5 to 75/25. 300 mg of the title compound is obtained as bright yellow oil.

IR (CHCl$_3$): 3610, 2925, 1738, 1725, 1573, 1453, 1260, 1040 cm$^{-1}$.

EXAMPLE 21

(4RS)-4-Hydroxy-5-{6-[(1E)-(3RS)-3-hydroxy-1-undecenyl]-2-pyridyl}-pentanoic acid A solution of 490 mg of 5-(6-bromo-2-pyridyl)-4-oxo-pentanoic acid methyl ester in 20 ml of methanol is mixed under ice cooling with 72 mg of sodium borohydride and stirred for 1 hour at 0–3° C. Then, 2 ml of acetone is added, stirred for 1 more hour and the reaction mixture is evaporated to dryness. The residue is distributed between water and ethyl acetate, the organic phase is dried on sodium sulfate and concentrated by evaporation. 421 mg of 5-[(6-bromo-2-pyridyl)-methyl]-tetrahydrofuran-2-one is obtained as yellow oil.

IR (CHCl$_3$): 1765, 1583, 1553, 1423, 1170, 1160, 1118, 1020, 985 cm$^{-1}$.

B. Under the conditions of example 11B, 400 mg of 5-[(6-bromo-2-pyridyl)-methyl]-tetrahydrofuran-2-one and 780 mg of (1E)-1-(tri-n-butylstannyl)-1-undecen-(3RS)-3-ol in 5 ml of dimethylformamide are reacted in the presence of 112 mg of 1,1'-bis-(diphenylphosphino)-ferrocene-palladium(ii) chloride as catalyst and worked up. The crude product is chromatographed on silica gel with hexane/0–30% ethyl acetate. 146 mg of 5-{6-[(1E)-(3RS)-3-hydroxy-1-undecenyl]-2-pyridyl-methyl}-tetrahydrofuran-2-one is obtained as yellow oil.

IR (CHCl$_3$): 2915, 2840, 1762, 1667, 1585, 1570, 1450, 1350, 1170, 970 cm$^{-1}$.

C. Under the conditions of example 2, 30 mg of 5-{6-[(1E)(3RS)-3-hydroxy-1-undecenyl]-2-pyridyl-methyl}-tetrahydrofuran-2-one in 2 ml of methanol is saponified with 1 ml of 1 n sodium hydroxide solution and worked up. 20 mg of the title compound is obtained as oil.

IR (CHCl$_3$): 3550–3080, 2920, 1724, 1585, 1570, 1450, 1255, 1090 cm$^{-1}$.

EXAMPLE 22

5-{6-(1E)-(3RS)-3-Hydroxy-1-undecenyl]-2-pyridyl-}-(4RS)-4-hydroxypentan-1-ol

A. A solution of 500 mg of 5-[(6-bromo-2-pyridyl)-methyl]-tetrahydrofuran-2-one in 13 ml of triethylamine and 2 ml of tetrahydrofuran is mixed with 350 mg of (3RS)-1-undecin-3-ol, 37 mg of bis-(triphenylphosphine)-palladium(II) chloride and 5 mg of copper(I) iodide and the mixture is stirred for 3 days at room temperature. The reaction mixture is evaporated to dryness, distributed between water and ethyl acetate, dried on sodium sulfate, concentrated by evaporation and the residue is chromatographed on silica gel with hexane/0–35% ethyl acetate. 294 mg of 5-{6-[(3RS)-3-hydroxy-1-undecinyl]-2-pyridyl-methyl}-tetrahydrofuran-2-one is obtained as oil.

IR (CHCl$_3$): 2920, 2850, 2220, 1768, 1585, 1450, 1173 cm$^{-1}$.

The production of (3RS)-1-undecin-3-ol is described in German patent application P 39 09 326.3.

B. A solution of 145 mg of 5-(6-[(3RS)-3-hydroxy-1-undecinyl]-2-pyridyl-methyl)-tetrahydrofuran-2-one in 1.2 ml of toluene is instilled in a solution of 0.725 ml of sodium-bis-(2-methoxyethoxy)-aluminum hydride (3.5 molar in toluene), which was diluted with 3.75 ml of toluene, under argon atmosphere at 0° C. After completion of the addition, the reaction mixture is stirred at room temperature and mixed after 3 hours under ice cooling in succession with 0.5 ml of isopropanol and 0.5 ml of water. The precipitate is suctioned off, washed with ethyl acetate, the filtrate is concentrated by evaporation and the residue is chromatographed on silica gel with methylene chloride/0–5% methanol. 22 mg of the title compound is obtained as yellow oil.

IR (CHCl$_3$): 3550–3080, 2920, 2859, 1585, 1570, 1450, 1255, 1180 cm$^{-1}$.

EXAMPLE 23

(5RS)-5-Hydroxy-5-{6-[(1E)-(3RS)-3-hydroxy-1-undecenyl]-2-pyridyl}-pentan-1-ol

A. A solution of 4 g of 2-bromo-6-[(1E)-(3RS)-3-hydroxy-1-undecenyl]-pyridine in 20 ml of dimethylformamide is mixed with 4.1 g of tert-butyldiphenylsilyl chloride and 2.1 g of imidazole and stirred for 15 hours at room temperature. The reaction mixture is poured into 100 ml of diethyl ether, shaken out twice with 20 ml of 1 n hydrochloric acid, 4 times with 20 ml of saturated common salt solution, dried on sodium sulfate and concentrated by evaporation. The residue is chromatographed on silica gel with hexane/0–5% ethyl acetate. 5.5 g of 2-bromo-6[(1E)-(3RS)-3-tert-butyldiphenylsilyloxy-1-undecenyl]-pyridine is obtained as oil.

IR (CHCl$_3$): 2925, 2850, 1578, 1548, 1426, 1110, 983, 820, 695 cm$^{-1}$.

B. 1.16 ml of n-butyllithium (1.6 molar in hexane) is instilled in a suspension of 500 mg of 2-bromo-6-[(1E)-(3RS)-3-tert-butyldiphenylsilyloxy-1-undecenyl]-pyridine in 2 ml of diethyl ether and 1 ml of tetrahydrofuran at −80° C. under argon atmosphere. After completion of the addition, the reaction mixture is stirred for 15 minutes at −40° C., cooled to −80° C. and mixed by instillation at this temperature with 140 mg of dimethylformamide. After 4 hours at −80° C., the reaction mixture is hydrolyzed with 3 ml of 2 n hydrochloric acid, the organic phase is separated, dried on sodium sulfate, concentrated by evaporation and the residue is chromatographed on silica gel with hexane/0–10% ethyl acetate. 385 mg of 6-[(1E)-(3RS)-3-tert-butyldiphenylsilyloxy-1-undecenyl]-pyridine-2-carbaldehyde is obtained as yellow oil.

IR (CHCl$_3$): 2915, 2845, 1705, 1768, 1580, 1450, 1420, 1105, 695 cm$^{-1}$.

C. 5.1 ml of a Grignard solution (produced from 385 mg of magnesium and 1.76 g of 4-chloro-1-tert-butyldimethylsilyloxybutane in tetrahydrofuran) is instilled at −80° C. in a solution of 370 mg of 6-[(1E)-(3RS)-3-tert-butyldiphenylsilyloxy-1-undecenyl]-pyridine-2-carbaldehyde in 3 ml of tetrahydrofuran. After 2 hours of stirring at −80° C., the reaction mixture is poured into 10 ml of saturated ammonium chloride solution, shaken out with ethyl acetate, the organic phase is dried and concentrated by evaporation. The residue is dissolved in 10 ml of tetrahydrofuran, mixed with 2.47 g of tetrabutylammonium fluoride and stirred for 17 hours at room temperature. The reaction mixture is poured into 50 ml of diethyl ether, washed with saturated common salt solution, dried on sodium sulfate and concentrated by evaporation. The residue is chromatographed on silica gel with hexane/0–30% ethyl acetate. 110 mg of the title compound is obtained as yellow oil.

IR (CHCl$_3$): 2920, 2850, 1590, 1570, 1455, 1258, 1075, 1015, 970 cm$^{-1}$.

EXAMPLE 24

2-[(2RS)-2-Hydroxy-2-(3-methoxycarbonylphenyl)-ethyl]-6[(1E)-(3RS)-3-hydroxy-1-undecenyl]-pyridine A. A solution of 15.1 g of 2,6-dibromopyridine in 500 ml of triethylamine is mixed under ice cooling with 10.2 g of 3-ethinylbenzoic acid methyl ester, 1.1 g of bis-(triphenylphosphine)-palladium(II) chloride ad 150 mg of copper(I) iodide and the mixture is stirred for 1 hour. Then, the ice bath is removed and it is stirred for 48 hours at room temperature. The precipitate is filtered off, the filtrate is evaporated to dryness, mixed with water and shaken out with ethyl acetate. The organic phase is dried on sodium sulfate, concentrated by evaporation and is chromatographed on silica gel with hexane/0–12% ethyl acetate. 4.8 g of 2-bromo-6[2-(3-methoxycarbonylphenyl)-ethinyl]-pyridine of melting point 124°–126° C. is obtained.

IR (CHCl$_3$): 2980, 2210, 1715, 1570, 1430, 1280, 1260, 1165, 1103 cm$^{-1}$.

B. A solution of 5.2 g of 2-bromo-6-[2-(3-methoxycarbonylphenyl)ethinyl]-pyridine in 30 ml of 60% sulfuric acid is heated to 140° C. with stirring for 1.5 hours. After cooling to room temperature, the reaction mixture is poured on ice water, the precipitate is suctioned off, and washed neutral with water. After drying at 50° C. in a vacuum, the crude product is dissolved in 35 ml of methanol, mixed with 3 drops of concentrated sulfuric acid and refluxed for 8 hours. Then, the reaction mixture is concentrated by-evaporation, distributed between water and ethyl acetate, the organic phase is washed with 10% sodium bicarbonate and water, dried on sodium sulfate and concentrated by evaporation. 3.5 g of 2-bromo-6-[(3-methoxycarbonylbenzoyl)-methyl]-pyridine of melting point 84°–86° C. is obtained.

IR (CHCl$_3$): 1720, 1633, 1590, 1438, 1300, 1165 cm$^{-1}$.

C. A solution of 2.4 g of 2-bromo-6-[2-(3-methoxycarbonylbenzoyl)-methyl]-pyridine in 100 ml of methanol is mixed under ice cooling with 293 mg of sodium borohydride, stirred for 1 hour at 0° C. and overnight at room temperature. Then, 3 ml of acetone is added, it is stirred for another half an hour and the reaction mixture is evaporated to dryness. The residue is distributed between water and ethyl acetate, the organic phase is dried with sodium sulfate and concentrated by evaporation. 2.33 g of 2-bromo-6-[(2RS)-2-hydroxy-2-(3-methoxycarbonylphenyl)-ethyl]-pyridine is obtained as yellow oil.

IR (CHCl$_3$): 3540–3280, 1715, 1585, 1550, 1434, 1285, 1104 cm$^{-1}$.

D. A solution of 120 mg of 2-bromo-6-[(2RS)-2-hydroxy-2-(3-ethoxycarbonylphenyl)-ethyl]-pyridine in 0.7 ml of toluene is mixed with 180 mg of (1E)-1-(tri-n-butylstannyl)-1-undecen-(3RS)-3-ol and 22 mg of 1,1'-bis-(diphenylphosphino)-ferrocene-palladium(II) chloride and stirred under argon atmosphere for 2 hours at 100° C. The reaction mixture is evaporated to dryness and the residue is chromatographed on silica gel with hexane/0–15% ethyl acetate. 56 mg of the title compound is obtained as oil.

IR (CHCl$_3$): 2920, 2850, 1715, 1500, 1450, 1285, 1260, 1090, 1005 cm$^{-1}$.

EXAMPLE 25

2-[(2RS)-2-Hydroxy-2-(3-carboxyphenyl)-ethyl]-6-[(1E)-(3RS)-3-hydroxy-1-undecenyl]-pyridine Under the conditions of example 2, 30 mg of 2-[(2RS)-2-hydroxy-2-(3-methoxycarbonylphenyl)-ethyl]-6-[(1E)-(3RS)-3-hydroxy-1-undecenyl]-pyridine in 2 ml of methanol is saponified with 1 ml of 1 n sodium hydroxide solution and worked up. 18 mg of the title compound is obtained as oil.

$^1$H-NMR (300 MHz, CD$_2$Cl$_2$, δ ppm): 0.80 (t,J=6 Hz,3H); 1.0–1.62 (14H); 2.95–3.17 (2H); 4.21–4.32 (1H); 5.08–5.20 (1H); 6.57–6.72 (2H); 6.90–6.98 (1H); 7.11–7.20 (1H); 7.32–7.42 (1H); 7.50–7.65 (2H); 7.82–7.93 (1H); 8.02–8.13 (1H).

EXAMPLE 26

2[(2RS)-2-Hydroxy-2-(3-hydroxymethylphenyl)-ethyl]-6-[(1E)(3RS)-3-hydroxy-1-undecenyl]-pyridine A. A solution of 180 mg of 2-bromo-6-[(2RS)-2-hydroxy-2-(3-methoxycarbonylphenyl)-ethyl]-pyridine in 4 ml of toluene is mixed under argon atmosphere at −70° C. with 0.88 ml of diisobutylaluminum hydride (20% in toluene) and-stirred for 3 hours at this temperature. The reaction mixture is mixed in succession at −70° C. with 0.3 ml of isopropanol and 0.3 ml of water and stirred overnight at room temperature. The precipitate is filtered off, the filtrate is dried on sodium sulfate and concentrated by evaporation. The crude product is dissolved in 3 ml of methanol, mixed with 82 mg of sodium borohydride and stirred overnight at room temperature. The reaction mixture is acidified to pH 1 with 2 n hydrochloric acid, shaken out with ethyl acetate, the organic phase is dried on sodium sulfate, concentrated by evaporation and the residue is chromatographed on silica gel with hexane/0-10% ethyl acetate. 103 mg of 2-bromo-6[(2RS)-2-hydroxy-2-(3-hydroxymethylphenyl)-ethyl]-pyridine is obtained as colorless oil.

IR (CHCl$_3$): 3680–3080, 2910, 2860, 1580, 1548, 1430, 1400, 1150, 1113, 1040, 788 cm$^{-1}$.

B. Under the conditions of example 24D, 96 mg of 2-bromo-6[(2RS)-2-hydroxy-2-(3-hydroxymethylphenyl)-ethyl]-pyridine and 160 mg of (1E)-1-(tri-n-butylstannyl)-1-undecen-(3RS)-3-ol in 1 ml of toluene is reacted in the presence of 1,1'-bis-(diphenylphosphino)-ferrocene-palladium(II) chloride as catalyst and worked up. The crude product is chromatographed on silica gel with hexane/0–25% ethyl acetate. 20 mg of the title compound is obtained as wine-red oil.

IR (CHCl$_3$): 2920, 2845, 1584, 1567, 1448, 1253, 1090, 1007 cm$^{-1}$.

EXAMPLE 27

5-{6-[(1E)-(3RS)-3-Hydroxy-1-undecenyl]-2-pyridyl}-4-pentynoic acid

A. Under the conditions of example 11B, 1.4 g of 5-(6-bromo-2-pyridyl)-4-pentynoic acid methyl ester and 5.75 g of (1E)-! -(tri-n-butylstannyl)-1-undecen-(3RS)-3-ol in 30 ml of dimethylformamide is reacted in the presence of 185 mg of 1,1'-bis-(diphenylphosphino)-ferrocene-palladium(II) chloride as catalyst and worked up. The crude product is chromatographed on silica gel with hexane/0–20% ethyl acetate. 354 mg of 5-(6[(1E)-(3RS)-3-hydroxy-1-undecenyl]-2-pyridyl)-4-pentynoic acid methyl ester is obtained as yellow oil.

IR (CHCl$_3$): 3030, 2400, 1740, 1520, 1430, 1218, 1048, 930 cm$^{-1}$.

B. Under the conditions of example 2, 20 mg of 5-{6-[(1E)(3RS)-3-hydroxy-1-undecenyl]-2-pyridyl}-4-pentynoic acid methyl ester in 1 ml of methanol is saponified with 2 ml of 1 n sodium hydroxide solution and worked up. 11 mg of the title compound is obtained as yellow oil.

IR (CHCl$_3$): 3690, 3040, 3020, 2930, 2860, 2400, 1730, 1605, 1260, 1100, 1015, 930 cm$^{-1}$.

We claim:

1. A leukotriene-B$_4$ analog of formula I

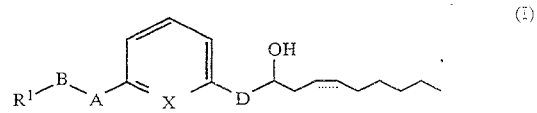

wherein

R$^1$ is a COOR$^2$ group, wherein R$^2$ is a C$_{2-4}$-alkyl group;

B is a C$_{1-3}$-alkylene group, a radical

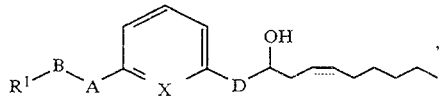, or a radical wherein R$^3$ is a hydrogen atom or a carboxy or methoxycarbonyl group;

A is —CH—, —O—, —C—, —NH—CO—, —CO—NH—,
       |           ||
       OH          O

—OCH$_2$—, —COCH$_2$—, or —CHOH—CH$_2$—;

X is N or CH;

D is 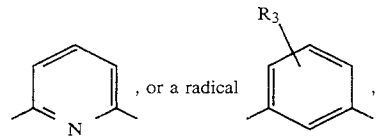

... is a single or double bond with the proviso that when B is C$_{1-3}$-alkylene, A is not —CHOH—CH$_2$—CO—NH—; or a salt thereof with a physiologically compatible base.

2. A process for the production of a leukotriene-B$_4$ analog of formula I

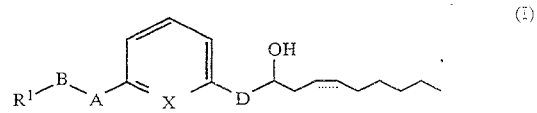

wherein

R$^1$ is COOR$^2$, wherein R$^2$ is a C$_{2-4}$-alkyl group;

B is a C$_{1-3}$-alkylene group, a radical

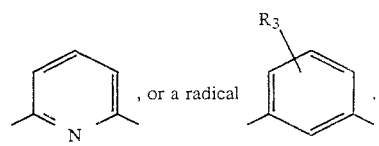, or a radical wherein R$^3$ is a hydrogen atom or a carboxy or methoxycarbonyl group;

A is —CH—, —O—, —C—, —NH—CO—,
       |           ||
       OH          O

—CO—NH—, —OCH$_2$—, —CH=CH—, —C≡C—, or —CHOH—CH$_2$—;

X is N or CH;

D is 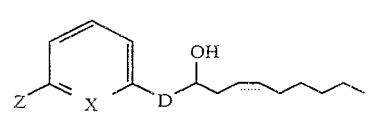

... is a single or double bond; or a salt thereof with a physiologically compatible base, comprising:

(a) a compound of formula II

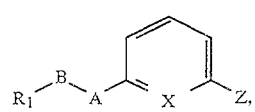

wherein D has the above-indicated meaning, ... is a single or double bond, X is a nitrogen atom, and Z is a bromine atom or an iodine atom, after reaction with n-butyllithium, is reacted with a compound of formula III

R$^1$—B—R$^4$      (III), wherein R$^l$ and B have the above-indicated meanings, and R$^4$ is —CHO or —COOCH$_3$, or (b) a compound of formula IV

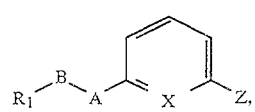

wherein $R^1$ B, A, and Z have the above-indicated meanings, and X is nitrogen, is reacted with a tri-n-butylstannane of formula V

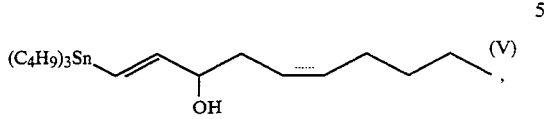
(V)

wherein ... is a single or double bond, in the presence of a palladium catalyst, or (c) a phenyl derivative of formula VI

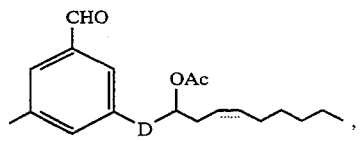
(VI)

wherein D is groups

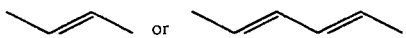 or 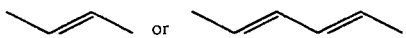,

AC is an acyl group with up to 8 C atoms, and ... is a single or double bond, is reacted with a Grignard compound of general formula VII

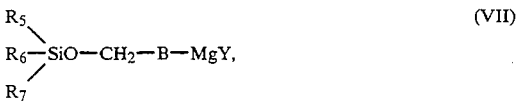
(VII)

wherein B has the above-mentioned meaning, Y is a chlorine atom or a bromine atom, and substituents $R_5$, $R_6$, and $R_7$ are the same or different and are $C_{1-4}$-alkyl groups or phenyl groups, the silyl ether is cleaved off, and the hydroxymethyl compound is oxidized to the carboxyl compound, the acyl groups and the carboxy group are esterified and optionally converted to its salts.

* * * * *